US012788033B2

(12) United States Patent
Gingras

(10) Patent No.: US 12,788,033 B2
(45) Date of Patent: Nov. 10, 2026

(54) DRINKING FORMULATION FOR MAINTAINING URINARY TRACT HEALTH IN CATS

(71) Applicant: LES PRODUITS VETWATER INC., Sainte-Brigide-d'Iberville (CA)

(72) Inventor: Pierre Luc Gingras, Sainte-Brigide-d'Iberville (CA)

(73) Assignee: LES PRODUITS VETWATER INC., Sainte-Brigide-d'Iberville (CA)

( * ) Notice: Subject to any disclaimer, the term of this patent is extended or adjusted under 35 U.S.C. 154(b) by 189 days.

(21) Appl. No.: 18/918,297

(22) Filed: Oct. 17, 2024

(65) Prior Publication Data

US 2025/0031728 A1 Jan. 30, 2025

Related U.S. Application Data

(63) Continuation of application No. 16/697,778, filed on Nov. 27, 2019, now abandoned.

(51) Int. Cl.

| | |
|---|---|
| *A23K 50/48* | (2016.01) |
| *A23K 20/20* | (2016.01) |
| *A61K 31/00* | (2006.01) |
| *C02F 1/04* | (2023.01) |
| *C02F 1/78* | (2023.01) |
| *A61K 9/00* | (2006.01) |

(52) U.S. Cl.

CPC .............. *A23K 50/48* (2016.05); *A23K 20/20* (2016.05); *A61K 9/0056* (2013.01); *A61K 9/0095* (2013.01); *A61K 31/00* (2013.01); *C02F 1/04* (2013.01); *C02F 1/78* (2013.01)

(58) Field of Classification Search

CPC ...... A23K 50/48; A23K 20/20; A61K 9/0056; A61K 9/0095; A61K 31/00; C02F 1/04; C02F 1/78; C02F 2103/026; C02F 1/68

See application file for complete search history.

*Primary Examiner* — Jeffrey T. Palenik

(74) *Attorney, Agent, or Firm* — Leveque Intellectual Property Law, P.C.

(57) ABSTRACT

The present disclosure relates to a liquid drinking formulation for consumption by pets, particularly cats, for preventing and/or treating urinary disorders, and stimulating water consumption. The drinking formulation comprises water that has less than 200 ppm of total minerals, and a pH between 5.9 and 7.0. Further described is a method for treating and/or preventing a urinary disorder, stimulating water consumption, and/or maintaining urinary health, in a pet, said method comprising administering the drinking formulation described herein to said pet.

11 Claims, 1 Drawing Sheet

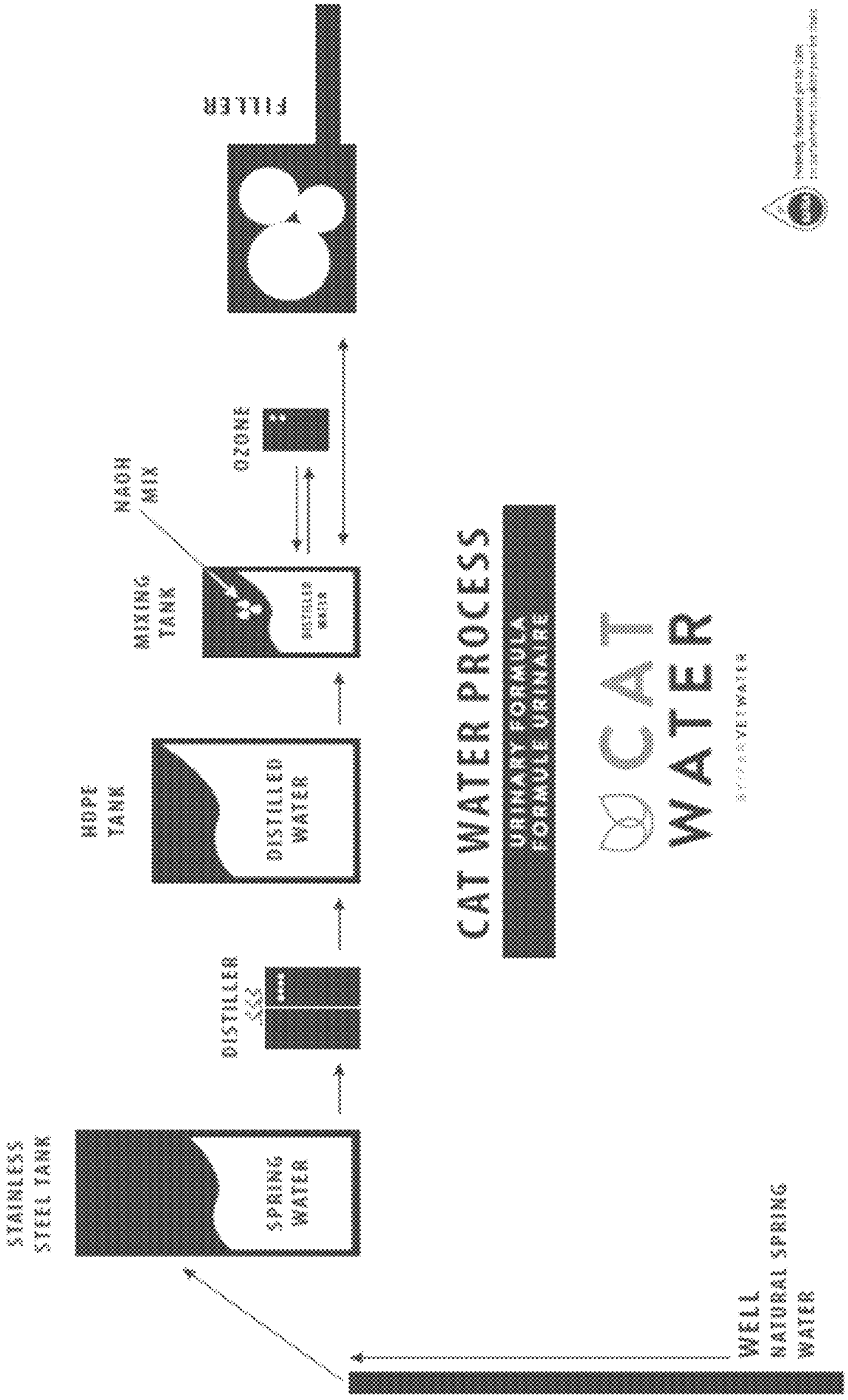
CAT WATER PROCESS
URINARY FORMULA
FORMULE URINAIRE
CAT
WATER
WELL
NATURAL SPRING
WATER
STAINLESS
STEEL TANK
SPRING
WATER
DISTILLER
HDPE
TANK
DISTILLED
WATER
MIXING
TANK
NAOH
MIX
OZONE
FILLER

DRINKING FORMULATION FOR MAINTAINING URINARY TRACT HEALTH IN CATS

CROSS-REFERENCE TO RELATED APPLICATIONS

This application is a continuation of U.S. patent application Ser. No. 16/697,778 filed on Nov. 27, 2019, the entire contents of which are hereby incorporated by reference.

FIELD OF THE INVENTION

The present invention relates to a drinking formulation for consumption by pets, particularly cats. Particularly, the drinking formulation stimulates water consumption and helps prevent and/or treat urinary disorders

BACKGROUND OF THE INVENTION

Feline urologic syndrome (FUS) or Feline Lower Urinary Tract Disease (FLUTD) remains a significant problem in household cats, with a morbidity rate of around 8% (Westropp et al., 2019; Segev et al. 2011). Symptoms include hematuria and pollakiuria, urinary tract infections, urothiliasis, urinary obstruction (UO), and stones in the bladder (Segev et al. 2011). Chronic symptoms occur in approximately 40-60% of cats. This is partly due to the lack of water consumption. It is well-known that in order to be attracted and willing to drink, cats are particularly sensitive to certain types of waters, thus certain factors such as freshness and taste in the water are important to consider. Furthermore, cats mostly consume water containing minerals, such as tap water, which are factors promoting the formation of stones and crystals in the kidneys and bladder. 60% of UO cases are attributed to urethral plugs, which include proteins, cellular debris, blood cells, and aggregates of crystalline minerals (e.g. calcium oxalate and struvite uroliths) (Segev et al. 2011). An alkaline urinary pH in cats (pH above 6.6) increases the risk of struvite urolith formaton, whereas an acidic urinary pH increases the risk of calcium oxalate urolith formation (Cottam et al., 2002). Managing cat diets, especially the type of foods and water, is important to maintain to a healthy urinary tract. An unhealthy urinary tract can further exacerbate UO caused by inflammation and persistent protein leakage into the urine. UO affects both female and male cats, but are more prevalent in males whose urinary tracts are longer and narrower. Treatment regimens are generally costly and include a flushing procedure, surgical removal of the stones, and/or lithotripsy (shockwaves to break down the stones).

We now have identified a drinking formulation to enhance and maintain urinary health of cats by providing said formulation which is sterile spring water and low in, or devoid of, minerals, chlorine, organic and inorganic contaminants, and has a slightly acidic pH around 6.2 to 6.4. This drinking formulation is slightly acidic while lacking minerals, enhancing the taste and stimulating consumption, thus helping prevent the formation of uroliths.

SUMMARY

A main aspect intended to be addressed by the present invention, is to provide a drinking formulation for pets, wherein said drinking formulation comprises water having less than 200 ppm of total mineral content and a pH between 5.9 and 7.0. Particularly, said drinking formulation is adapted to maintain urinary health, prevent and/or treat a disorder, and/or stimulate water consumption in pets.

In another aspect intended to be addressed by the present invention, is to provide a drinking formulation for use in maintaining urinary health in pets, wherein said drinking formulation comprises water having less than 200 ppm of total mineral content and a pH between 5.9 and 7.0

In another aspect intended to be addressed by the present invention, is to provide a drinking formulation for use in treating a urinary disorder in pets, wherein said drinking formulation comprises water having less than 200 ppm of total mineral content and a pH between 5.9 and 7.0.

In another aspect intended to be addressed by the present invention, is to provide a drinking formulation for use in preventing a urinary disorder in pets, wherein said drinking formulation comprises water having less than 200 ppm of total mineral content and a pH between 5.9 and 7.0.

In another aspect intended to be addressed by the present invention, is to provide a use of a drinking formulation as described herein, for the treatment of a urinary disorder in a pet.

In another aspect intended to be addressed by the present invention, is to provide a use of a drinking formulation as described herein, for the prevention of a urinary disorder in a pet.

In another aspect intended to be addressed by the present invention, is to provide a use of a drinking formulation as described herein, for maintaining urinary health in a pet.

In another aspect intended to be addressed by the present invention, is to provide a use of a drinking formulation as described herein, for stimulating water consumption in a pet.

In another aspect intended to be addressed by the present invention, there is provided a method for treating and/or preventing a urinary disorder, and/or maintaining urinary health, in a pet, said method comprising administering a drinking formulation to said pet, wherein said drinking formulation comprises water having less than 200 ppm of total mineral content and a pH between 5.9 and 7.0.

DESCRIPTION

DESCRIPTION OF THE FIGURES

FIG. 1 shows the process of manufacturing one embodiment of the drinking formulation of the present invention.

ABBREVIATIONS AND DEFINITIONS

Abbreviations

Definitions

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "about" or "around" as used herein refers to a margin of + or −10% of the number indicated. For sake of precision, the term about when used in conjunction with, for example: 90% means 90%+/−9% i.e. from 81% to 99%. More precisely, the term about refers to + or −5% of the number indicated, where for example: 90% means 90%+/−4.5% i.e. from 86.5% to 94.5%. When used in the context of a pH, the term about means+/−0.5 pH unit.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" as used herein refers to an animal, and most preferably a pet who is the object of treatment, prevention or maintenance.

"Pet" includes domestic animals such as laboratory animals and household pets, (such as, for example, cats, dogs, rats, ferrets, swine, cattle, sheep, goats, horses, rabbits, etc.).

As used herein, the terms "free of" or "devoid of" are used herein to indicate that the composition comprises 10 ppm (or mg/L) or less, less than 9 ppm, less than, 8 ppm, less than 7 ppm, less than 6 ppm, les than 5 ppm, less than 4 ppm, less than 3 pmp, less than 2 ppm, less than 1 ppm, or 0 ppm of a certain chemical or molecule, such as minerals, chlorine, and contaminants. Such chemicals or molecules can be measured and analyzed using a spectrophotometer, nuclear magnetic resonance (NMR), or by chromatography (for example LC-MS or HPLC).

As used herein, the term "trace" is used herein to indicate trace amounts or a low concentration of a chemical or molecule comprised in a composition, measuring between 1 to 200 ppm, particularly between 1 and 100 ppm, more particularly between 1 and 50 ppm, still more particularly between 1 and 20 ppm, most particularly between 1 and 10 ppm.

DETAILED DESCRIPTION OF PARTICULAR EMBODIMENTS

Drinking Formulation

In some aspects, the present description relates to a drinking formulation for use in increasing water consumption, maintaining urinary health, and/or preventing or treating urinary disorders in pets, said formulation comprising water having less than 200 ppm of total minerals and a pH between 5.9 and 7.0.

Particularly, the water has less than 100 ppm of mineral content; more particularly less than 50 ppm, still more particularly less than 20 ppm and most particularly, less than 10 ppm of mineral content.

Still, according to a particular embodiment, the water is free of minerals. More particularly, the water has less than 9, 8, 7, 6, 5, 4, 3, 2, or even less than 1 ppm of total mineral content. Most particularly the water has 0 ppm of total mineral content.

In some aspects, the drinking formulation comprises water from a natural source, such as, for example, spring water.

In some aspect, the drinking formulation comprises water that is sterilized.

In some aspects, the drinking formulation comprises water that is distilled. In some aspects, the water is distilled by evaporation.

In some aspects, the drinking formulation comprises water that is ozonated. In some aspects, the water is ozonated by an ozonator.

In some aspects, the water can be sterilized by distillation, use of filters (e.g. carbon filtration, microporous filtration, ultrafiltration), reverse osmosis and/or ozonation.

In some aspects, the water can be demineralized (i.e. deionized) by distillation, ion exchange, electrodeionization, ultraviolet oxidation, or electrodialysis use of filters (e.g. carbon filtration, microporous filtration, ultrafiltration), and/or reverse osmosis.

In some aspects, the drinking formula comprises less than 15 ppm, 10 ppm, 5 ppm, or 1 ppm of organic or inorganic pollutants or contaminants.

In some aspects, the drinking formula comprises 0 ppm of organic or inorganic pollutants or contaminants.

In some aspects, the drinking formula comprises less than 25 ppm, 20 ppm, 15 ppm, 10 ppm, 5 ppm, or 1 ppm of chlorine.

In some aspects, the drinking formula comprises 0 ppm of chlorine.

In some aspects, the drinking formulation has a pH that is between 5.9 and 6.9, between 5.9 and 6.8, between 5.9 and 6.7, between 6.0 and 6.6, or between 6.1 and 6.5.

In some aspects, the drinking formulation has a pH that is between 6.2 and 6.4.

In some aspects, the pH is adjusted with a concentrated acidic or alkaline solution. In some aspects, the pH is adjusted with NaOH (e.g. 50% aqueous solution).

Uses and Methods of Use

In some aspects, the present description relates to the use of a drinking formulation defined herein for the treatment of urinary disorders in a pet.

In some aspects, the present description relates to the use of a drinking formulation defined herein for the prevention of urinary disorders in a pet.

In some aspects, the present description relates to the use of a urinary formulation defined herein for maintaining urinary health in a pet.

In some aspects, the present description relates to the use of a drinking formulation defined herein for stimulating water consumption in a pet. In some aspects, the water consumption is stimulated. In some aspects, the consumption of water is optimized to about 50 ml/kg/day in cats.

Method of Treatment

In some aspects, the present description relates to a method for treating and/or preventing a urinary disorder, and/or maintaining urinary health, in a pet, said method comprising administering a drinking formulation to said pet, wherein said drinking formulation as is defined herein.

Urinary Disorders

In some aspects, the urinary disorder is any disorder, disease, or abnormality involving any component of the urinary system, such as the kidneys, ureters, bladder, and the urethra. In some aspects, the urinary disorder is Feline urologic syndrome (FUS) or Feline Lower Urinary Tract Disease (FLUTD).

In some aspects, the urinary disorder comprises hematuria and pollakiuria, severe chronic and recurrent inflammation, urinary tract infections, urothiliasis, urinary obstruction (UO), and stones in the urinary tract, bladder or kidney. In some aspects, the urinary obstruction comprises the formation of uroliths or stones, such as crystalline minerals like calcium oxalate or struvite stones. In some aspects, the urinary disorder is caused by lack of consumption of water or increased mineral consumption.

Pet

In accordance with an alternative embodiment of the method and/or use of the drinking formulation as defined herein, the pet is, for example: a household animal or a farm animal.

More particularly, the household pet may be a dog, a cat or a rodent (such as for example a rat of a ferret), and the farm animal may be a horse, a donkey, a pig, a cow, a sheep, or a goat.

More particularly, the pet is a cat.

EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1—Method of Production of Drinking Formulation

Spring water from is collected from a well in the province of Quebec, Canada and is distilled. Water is heated to 105.6° C. in a water distiller. Steam is collected and condensed into liquid water, removing any chemical contaminants (e.g. heavy metals, chlorine and nitrates), microorganisms, and minerals. Distilled water is then stored in high density polyethylene tanks (HDPE). The pH of distilled water is adjusted to 6.2-6.4 with an aqueous solution of 50% NaOH. Distilled water is then further disinfected by ozonation. pH is then readjusted to 6.2-6.4, if necessary, and stored (FIG. 1).

Example 2—Composition of Drinking Formula

The pH and mineral content of the drinking formulation is shown in Table 1.

TABLE 1

| pH, Nutrition Facts and Composition of Drinking Formulation | |
|---|---|
| pH | 6.2-6.4 |
| Calories | 0 |
| **Composition (mg/L or ppm)** | |
| Total Dissolved Mineral Salts | <6 |
| Total Fat | 0 |
| Total Carbohydrates | 0 |
| Total Protein | 0 |
| As | 0 |
| Ca | 0 |
| Cl | 0 |
| Cu | 0 |
| F | 0 |
| $HCO_2$ | 0 |
| K | 0 |
| Mg | 0 |
| $NO_4$ | 0 |
| Na | <4 |
| Pb | 0 |
| $SO_4$ | 0 |
| Zn | 0 |

Example 3—Advantages of Drinking Formulation

In order to treat or prevent the formation of bladder stones causing UO in cats, a healthy urinary tract must be maintained. This is achieved by increasing the consumption of water, controlling urinary pH levels, and reducing the consumption of minerals. Being distilled water from a natural spring source and being relatively free of chemical contaminants and impurities, the taste of the present drinking formulation of Table 1 (Catwater™) has an element of freshness, which is an important factor especially in cats who are very particular.

Since cats are carnivores, it has been shown that they prefer the taste of meat, which has an acidic pH (Little et al., 2012). Thus, the slight acidity of Catwater™ is shown to enhance the taste and stimulates the consumption of water. Furthermore, taste buds detecting acidity are the second most abundant in cats, after those detecting amino acids. Since the pH of Catwater™ is around 6.2 to 6.4, it is desired to maintain the urinary pH around a similar range. This pH range also reduces the formation of struvite (form at more alkaline pH) and calcium oxalate (form at more acidic pH) uroliths. In comparison, tap water, which is the most common source of water for household cats, contains traces of chemical contaminants, has an alkaline pH and is not demineralized (Table 2). Sources of water may be demineralized by filtration and reverse osmosis. However, most filters do not completely remove mineral deposits in the water. Furthermore, reverse osmosis of water is not economical since the system is costly and the process itself is very wasteful. Reverse osmosis can also contaminate the water by microbial attachment to the membrane surface and leaking through the filter (Malaeb et al., 2011). Therefore, these sources of water require pretreatment with chlorine, thereby affecting taste.

TABLE 2

Functions and advantages of Catwater ™ and other sources of water

| Function | Catwater ™ | Tap Water | Filtered Water | Spring Water (untreated) | Demineralized Water |
|---|---|---|---|---|---|
| Increasing consumption of water | Yes<br>Natural spring water that is | No<br>Traces of chemicals | No<br>Traces of chemicals | No<br>Chlorine-free but | No<br>Too acidic |

TABLE 2-continued

Functions and advantages of Catwater ™ and other sources of water

| Function | Catwater ™ | Tap Water | Filtered Water | Spring Water (untreated) | Demineralized Water |
|---|---|---|---|---|---|
| | slightly acidic, ozonated, and chlorine-free to enhance the taste | like chlorine, mercury, lead, pesticides, etc. | like chlorine, mercury, lead, pesticides, etc. | alkaline water | |
| Controlling urinary pH levels | Yes pH of 6.2-6.4, optimal urinary pH levels | No pH of 7.2-7.8, too alkaline | No pH of 7.1, too alkaline | No pH of 7.2-7.8, too alkaline | No pH of 5.3 to 5.8, too acidic |
| Prevent or treat crystal and urinary stone formation in the bladder | Yes Mineral-free water (less than 6 ppm) | No Contains minerals | No Contains traces of minerals | No Contains minerals | Yes Demineralized by reverse osmosis but susceptible to contamination |

Example 4: Clinical Trial in Cats

To determine the effect of Catwater™ in preventing urinary disorders, a 60-day cross-over design clinical trial is conducted.

The trial consists of a cohort of 16 adult cats divided in 2 groups of 8, kept in two separate rooms. One group consumes only Catwater™ and the second group consumes only tap water, as a water source. Both groups are fed the same food diet.

The trial is conducted for a period of 30 days, at which point the two groups are crossed over for another 30 days. Therefore, the Catwater™ group is switched to tap water as the water source, and the tap water group is switched to Catwater™. Total water intake, total urine output and urine specific gravity (USG), mineral levels in the urine and other parameters are measured weekly.

Results are expected that, while drinking Catwater™, water consumption is stimulated, voiding a larger volume of urine with a lower USG, and lower mineral levels. The urinary pH is also expected to decrease.

REFERENCES

Westropp, J. L. et al. Chronic Lower Urinary Tract Signs in Cats. *Vet. Clin. Small Anim.* (2019) 49:187-209.

Segev, G. et al. Urethral obstruction in cats: predisposing factors, clinical, clinicopathological characteristics and prognosis. *Journal of Feline Medicine and Surgery.* (2011) 13:101-108.

Cottam, Y. H. et al. Feline Reference Values for Urine Composition. *The Journal of Nutrition.* (2002) 132:6, 1754S-1756S.

Malaeb, L. Reverse osmosis technology for water treatment: State of the art review. *Desalination.* (2011) 267:1-8.

Little, E. S. *The Cat, Clinical Medicine and Management* (2012) pp 193, 237.

The invention claimed is:

1. A method for treating a urinary disorder, maintaining urinary health, and/or increasing water consumption in a pet, said method comprising administering a drinking formulation to said pet, wherein said drinking formulation consists of distilled and ozonated water having less than 200 ppm of total mineral content, having a pH between 6.2 and 6.4, having less than 15 ppm of organic or inorganic pollutants or contaminants, and being free of chlorine.

2. The method of claim 1, wherein the pH is between 6.2 and 6.3.

3. The method of claim 1, wherein the pH is between 6.3 and 6.4.

4. The method of claim 1, wherein the water has less than 150 ppm, 100 ppm, 50 ppm, 25 ppm, 20 ppm, 15 ppm, 10 ppm, 7 ppm, 6 ppm, 5 ppm, 4 ppm, 3 ppm, 2 ppm, or 1 ppm of total mineral content.

5. The method of claim 1, wherein the water is demineralized or has 0 ppm of total mineral content.

6. The method of claim 1, wherein the water has less than 10 ppm, 5 ppm, or 1 ppm of chlorine.

7. The method of claim 1, wherein the water has 0 ppm of chlorine.

8. The method of claim 1, wherein the water has less than 10 ppm, 5 ppm, or 1 ppm of organic or inorganic pollutants or contaminants.

9. The method of claim 1, wherein the water has 0 ppm of organic or inorganic pollutants or contaminants.

10. The method of claim 1, wherein the water used to form the drinking formulation is sourced from spring water.

11. The method of claim 1, wherein the pet is a cat.

* * * * *